United States Patent
Schoenbeck

(10) Patent No.: US 8,956,477 B2
(45) Date of Patent: Feb. 17, 2015

(54) METHOD OF MAKING A WEB FROM WHICH ELASTIC DIAPER CLOSURES CAN BE STAMPED

(75) Inventor: Marcus Schoenbeck, Versmold (DE)

(73) Assignee: Mondi Consumer Packaging Technologies GmbH, Gronau (DE)

( * ) Notice: Subject to any disclaimer, the term of this patent is extended or adjusted under 35 U.S.C. 154(b) by 275 days.

(21) Appl. No.: 13/597,673

(22) Filed: Aug. 29, 2012

(65) Prior Publication Data

US 2013/0230700 A1 Sep. 5, 2013

(30) Foreign Application Priority Data

Aug. 31, 2011 (EP) .................................. 11179475

(51) Int. Cl.
| | |
|---|---|
| *B32B 37/00* | (2006.01) |
| *A61F 13/15* | (2006.01) |
| *A61F 13/62* | (2006.01) |
| *B29C 65/08* | (2006.01) |
| *B29C 65/00* | (2006.01) |
| *B29C 65/50* | (2006.01) |
| *B32B 5/02* | (2006.01) |
| *B32B 5/04* | (2006.01) |
| *B29C 65/48* | (2006.01) |
| *B29L 31/48* | (2006.01) |
| *B29C 65/02* | (2006.01) |

(52) U.S. Cl.
CPC .......... *A61F 13/15577* (2013.01); *A61F 13/62* (2013.01); *B29C 65/086* (2013.01); *B29C 66/83411* (2013.01); *B29C 66/83413* (2013.01); *B29C 65/5021* (2013.01); *B29C 65/5057* (2013.01); *B29C 66/43* (2013.01); *B29C 66/712* (2013.01); *B29C 66/7294* (2013.01); *B29C 66/81433* (2013.01); *B32B 5/022* (2013.01); *B32B 5/04* (2013.01); *B29C 65/4815* (2013.01); *B29L 2031/4878* (2013.01); *B29C 66/71* (2013.01); *B29C 65/02* (2013.01); *B29C 65/087* (2013.01); *B29C 2793/009* (2013.01)
USPC .......................................... 156/73.1; 156/290

(58) Field of Classification Search
USPC ............... 156/73.1, 290, 308.2, 580.1, 580.2; 264/442, 443, 444, 445
See application file for complete search history.

(56) References Cited

U.S. PATENT DOCUMENTS

| | | | |
|---|---|---|---|
| 6,051,094 | A | 4/2000 | Melbye |
| 6,255,236 | B1 | 7/2001 | Cree |

(Continued)

FOREIGN PATENT DOCUMENTS

DE 102004035649 A 3/2006

*Primary Examiner* — James Sells
(74) *Attorney, Agent, or Firm* — Andrew Wilford

(57) ABSTRACT

Elastically stretchable diaper closure elements that each comprise an inelastic and reinforced attachment region for securing a closure component and an adjacent elastic stretch region can be punched from a textile web. A plurality of pairs of elastic film strips of an elastically stretchable polymer are inserted between two cover layers of nonwoven with the film strips parallel and spaced laterally from one another. Between each pair of elastic film strips a strip of a reinforcement film is inserted that has a support layer and an outer layer of polyethylene on at least one side between the cover layers with each reinforcement-film strip overlapping each of the respective elastic film strips at a respective overlap region. The reinforcement-film strips are bonded to the elastic film strips in the overlap regions, and the nonwoven cover layers are bonded to the reinforcement film strips by ultrasonic or thermal welding.

11 Claims, 3 Drawing Sheets

(56) References Cited

U.S. PATENT DOCUMENTS

| | | | |
|---|---|---|---|
| 6,652,696 B2* | 11/2003 | Kuen et al. | 156/204 |
| 6,875,710 B2 | 4/2005 | Eaton | |
| 7,959,619 B2* | 6/2011 | Cartier et al. | 604/385.01 |
| 8,716,549 B2* | 5/2014 | Cheng et al. | 604/378 |
| 2003/0051804 A1 | 3/2003 | Wood | |

\* cited by examiner

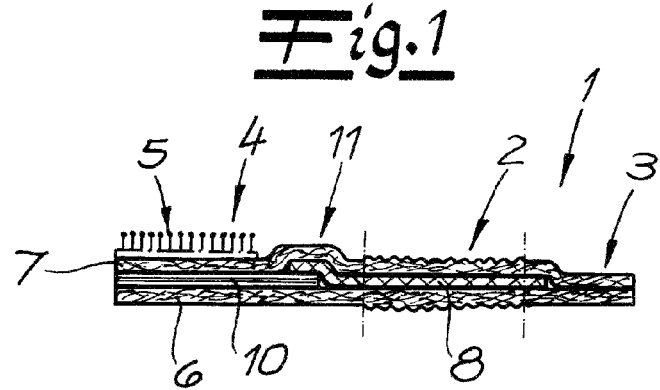
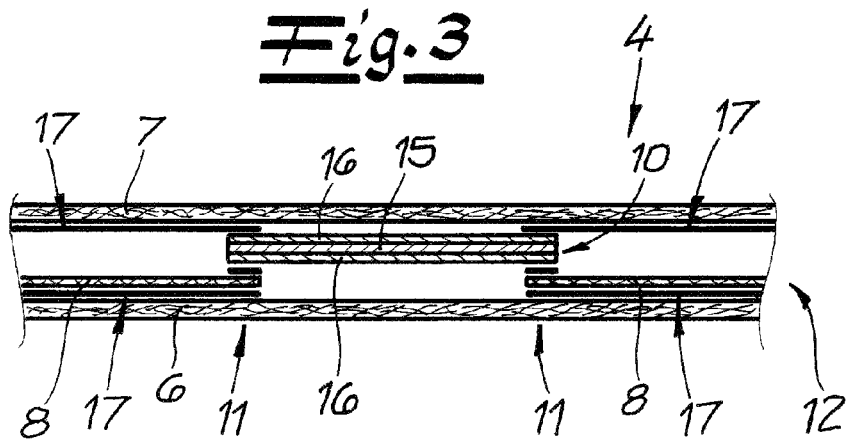
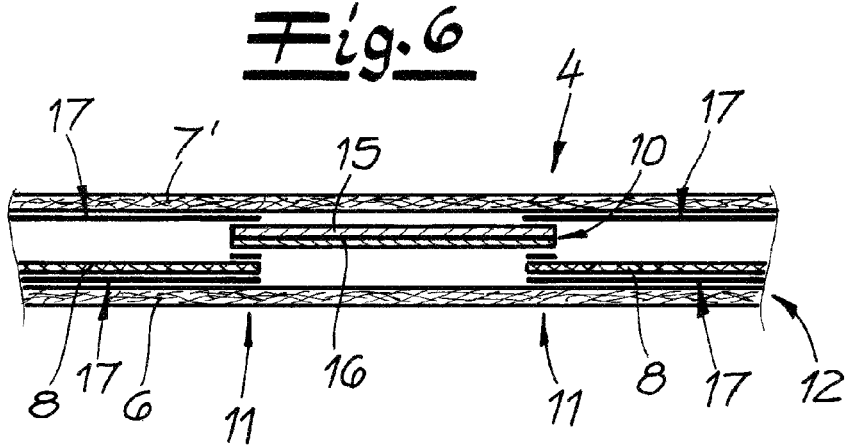

METHOD OF MAKING A WEB FROM WHICH ELASTIC DIAPER CLOSURES CAN BE STAMPED

FIELD OF THE INVENTION

The present invention relates to the manufacture of diaper closures. More particularly this invention concerns a web specifically usable for such manufacture.

BACKGROUND OF THE INVENTION

A typical elastically stretchable diaper closure elements each comprises an inelastic and reinforced attachment region to which a closure component can be attached. It is punched from a textile web having parallel and mutually spaced film strips composed of an elastically stretchable polymer laminated between two cover layers of nonwoven textile.

DE 10 2004 035 649 discloses a method for producing diaper closure elements. The nonwoven webs are glued directly to each other in regions between the elastic film strips. The diaper closure elements punched out of the textile web each have an elastic stretch region and two bilaterally flanking attachment regions of nonwoven. The diaper closure elements can be in the form of strips or have the form of so-called diaper ears, the attachment region of which on one diaper is wider than the attachment region for attaching the closure component. Strong forces are transferred through the closure component to the diaper closure element. A rigid attachment region with high tensile strength is advantageous in terms of a uniform application of force to the diaper closure element. In addition, care must be taken that the attachment regions composed of nonwoven not fray or plastically stretch when the diaper closure elements are stretched up to the elastic limit of the elastic range in use.

U.S. Pat. No. 6,255,236 discloses a diaper closure element that has an elastic film as the core layer and nonwoven layers laminated onto the core layer. The nonwoven layers and the core layer are of identical outside dimensions, i.e. the elastic core layer in the stretch direction is of the same width as the bilaterally laminated layers of nonwoven. Both the attachment region for the closure component and the attachment region for securing to a diaper are reinforced by a layer of an inelastic polymer. Reinforcement is effected by a high-tensile-strength film, for example of a polypropylene homopolymer, that is laminated in the attachment regions between the elastic film and one of the two cover layers, and that restricts the elasticity of the elastic core layer. Since elastic polymers are expensive materials, there is a need to keep the relative proportion of elastic polymer in the composite material as low as possible without this negatively affecting the elasticity and mechanical properties of the composite material U.S. Pat. No. 6,051,094 discloses a diaper closure element that has a backing comprising elastic and inelastic regions. The backing is composed, in particular, of a coextruded film comprising an elastic core layer and inelastic cover layers. A textile is laminated to one face of the backing. A closure component is attached to the other face of the backing. An elastic stretch region is generated by local stretching in which the inelastic cover layers of the backing and the laminated nonwoven are overstretched in certain regions. This is characterized as selective mechanical activation. The other disadvantageous aspect here is that the elastic backing extends across the entire width of the diaper closure element having the inelastic attachment regions. A further disadvantageous aspect is that the diaper closure element has a textile surface only on one side.

U.S. Pat. No. 6,875,710 describes a diaper closure element comprising a textile backing composed for example of a nonwoven. The backing is reinforced in predetermined regions by a layer of an inelastic polymer applied in a thermoplastic state so as to infiltrate at least part of the fiber structure of the nonwoven layer. In another region located at a spacing therefrom, the backing has a coating of a thermoplastic elastomer that also infiltrates at least part of the fiber structure of the nonwoven and creates an elastic stretch region. If the material is stretched up to the elastic limit of the elastic range, there is the risk that the textile composed exclusively of nonwoven will be plastically deformed and destroyed between the elastic region and the inelastic regions.

OBJECTS OF THE INVENTION

It is therefore an object of the present invention to provide an improved method of making a web from which elastic diaper closure can be punched.

Another object is the provision of such an improved method of making such a web that overcomes the above-given disadvantages, in particular that facilitates the production of inexpensive and durable diaper-closure elements.

SUMMARY OF THE INVENTION

Elastically stretchable diaper closure elements that each comprise an inelastic and reinforced attachment region for securing a closure component and an adjacent elastic stretch region can be punched from a textile web. According to the invention a plurality of pairs of elastic film strips of an elastically stretchable polymer are inserted between two cover layers of nonwoven with the film strips parallel and spaced laterally from one another. Between each pair of elastic film strips a strip of a reinforcement film is inserted that has a support layer and an outer layer of polyethylene on at least one side between the cover layers with each reinforcement-film strip overlapping each of the respective elastic film strips at a respective overlap region. The reinforcement-film strips are bonded to the elastic film strips in the overlap regions, and the nonwoven cover layers are bonded to the reinforcement film strips by ultrasonic or thermal welding. The cover layer bonded to the outer polyethylene layer of the reinforcement film itself is composed of bicomponent fibers that have a fiber core of polypropylene and a fiber sheath of polyethylene. The support layer of the reinforcement film is composed of a polymer that has a higher melting point than the polyethylene of the outer layer.

The support layer of the reinforcement film is composed of a polymer that is characterized by greater rigidity and tensile strength than the elastic film strip, and has a higher melting point than the polyethylene of the outer layer. The support layer is preferably composed of a polypropylene, in particular, polypropylene homopolymer. In addition, cycloolefin copolymers, styrene polymers, polyamides, polyactides, thermoplastic polyurethanes, as well as blends of the referenced polymers are suitable for use as the support layer.

The outer layer of the reinforcement film of polyethylene is permanently bonded at the thermally or ultrasonically generated welding points to the polyethylene sheaths of the bicomponent fibers forming the nonwoven cover layer. Local melting enables the materials to form a permanent bond such that a uniform pattern of punctiform, ellipsoid, or rod-shaped junctions is created. A low input of energy for the ultrasonic or thermal welding is sufficient due to the low melting point of polyethylene. The ultrasonic welding is done in such a way that neither the support layer of the reinforcement film nor the polypropylene core of bicomponent fibers is melted. This situation is analogous when using thermal welding. The fiber core of polypropylene ensures that the fibers retain their structure and are not destroyed. In particular, low-density polyethylene (LD-PE), low-density linear polyethylene (LLD-PE), or very-low-density polyethylene (VLD-PE) can be employed both for the outer layer of reinforcement film composed of polyethylene and also for the sheath material of bicomponent fibers of the nonwoven cover layer.

The polyethylenes have a melt temperature ranging between 105° C. and 145° C., whereas the melt temperature of polypropylene is higher. In those textile regions that create a rigid and high-tensile-strength attachment region for the closure components, the support layer of the reinforcement film provides the material with the desired mechanical properties, and in particular, determines the tear resistance and rigidity of this region. It is obvious that the support layer of the reinforcement film must have a sufficient layer thickness so as to achieve the desired reinforcement, whereas the outer layer of the reinforcement film only needs to ensure a reliable thermal bond with the cover layer composed of nonwoven. The outer layer of the reinforcement film composed of polyethylene advantageously has a layer thickness of between 2 and 20 µm, while the support layer provided for reinforcement should have a thickness of between 20 and 100 µm.

The cover layer composed of bicomponent fibers of the core/sheath type has more beneficial usage properties than a nonwoven composed of polypropylene fibers. The polyethylene components of the bicomponent fibers improve the toughness and elongation to rupture of the nonwoven, and provide the nonwoven with improved frictional and wear properties. The nonwoven composed of bicomponent fibers, in which the fibers comprise a fiber core of polypropylene and an fiber sheath of polyethylene, retains its fiber structure when the textile web is mechanically activated to improve elasticity. During mechanical activation, the textile web is passed through an arrangement of shaped rolls that act on the elastic stretch regions of the textile web, and overstretches them locally to such a degree that the polypropylene fibers tear. The tougher polyethylene sheath of the bicomponent fibers enables the fiber structure to be maintained despite the overstretching during mechanical activation.

The reinforcement film can be composed of a coextruded film whose support layer is composed of polypropylene and is bonded to a nonwoven composed of polypropylene fibers. In this embodiment of the method according to the invention, a textile web is generated that has two differently formed cover layers. A first cover layer is composed of a nonwoven of bicomponent fibers that has a fiber core of polypropylene and a fiber sheath of polyethylene. A second cover layer that is bonded directly to the support layer is composed of a nonwoven of polypropylene fibers. The adhesion of the first cover layer to the polyethylene layer of the reinforcement film is higher than the adhesion of the bond between the nonwoven layer composed of polypropylene and the support layer, also composed of polypropylene, of the reinforcement film. A precise reduction in the adhesion on one side of the reinforcement film can have a positive effect on the tear resistance of the laminate.

The reinforcement film can have one or more layers between the support layer of polypropylene and the outer polyethylene layer. In particular, the reinforcement film can is have an outer polyethylene layer, a support layer of polypropylene, and an intermediate layer to provide reinforcement from a stiff polymer.

The reinforcement film can also be composed of a multilayer film that has the support layer as the core and an overlay of polyethylene on both sides. Nonwovens composed of bicomponent fibers are employed for both cover layers, which fibers have a fiber core of polypropylene and a fiber sheath of polyethylene. The input of energy is adjusted in such a way that the contact surfaces composed of polyethylene at least initially melt or fuse, such that an intimate bond is generated between the sheaths of the bicomponent fibers and the flanking polyethylene overlay of the reinforcement film. This results in an especially secure anchoring of the reinforcement film in the nonwoven cover layers.

The elastic film strips are preferably glued to the cover layers composed of nonwoven. Ultrasonic or thermal welding is restricted to those regions of the laminate that are subjected to strong peel forces when the diaper closure is handled.

According to another embodiment of the method according to the invention the reinforcement film is glued to the elastic film strips in the bilateral overlap regions. The adhesive bond in the overlap regions subsequently facilitates ultrasonic welding. Ultrasonic welding involves passing the cover layers composed of nonwoven and the reinforcement film between a sonotrode and a pixel roll whose the roll surface has a structure consisting of bumps and indentations. Fibers can accumulate at the intake gap. Gluing the textile layers to be bonded to each other at the edge facilitates delivery of the material into the intake region between sonotrode and pixel roll. In order to prevent any folding from occurring, it may be advantageous to attach the reinforcement film to at least one cover layer by an adhesive that has been applied in stripes before the reinforcement film has been permanently bonded by ultrasonic welding to the two cover layers.

Sonotrodes are used for the ultrasonic welding, the sonotrodes being set into sympathetic vibration by introducing high-frequency mechanical vibrations. The sonotrode acts on a pixel roll whose surface has a structure composed of bumps and indentations. The surface structure of the pixel roll determines the shape and arrangement of the weld points. The method according to the invention can be implemented by a sonotrode that has a smooth contact surface. There is the risk that molten polyethylene can be deposited on the sonotrode if the energy input into the laminate is excessive. The deposits can form long streaks that eventually detach and contaminate the textile web. The risk of material accumulating between the sonotrode and the pixel roll is reduced by using a sonotrode that is cylindrical and rotatable. The use of a rotatable sonotrode therefore constitutes a preferred embodiment of the method according to the invention.

BRIEF DESCRIPTION OF THE DRAWING

The above and other objects, features, and advantages will become more readily apparent from the following description, reference being made to the accompanying drawing in which:

FIG. 1 is a schematic longitudinal section in the stretch direction through an elastic diaper closure element that has an inelastic and reinforced attachment region that enables a closure component to be attached;

FIG. 3 shows the layered structure of the textile web in an inelastic and reinforced attachment region;

FIG. 6 shows a variant of the layered structure shown in FIG. 3.

DETAILED DESCRIPTION

Figure 2:
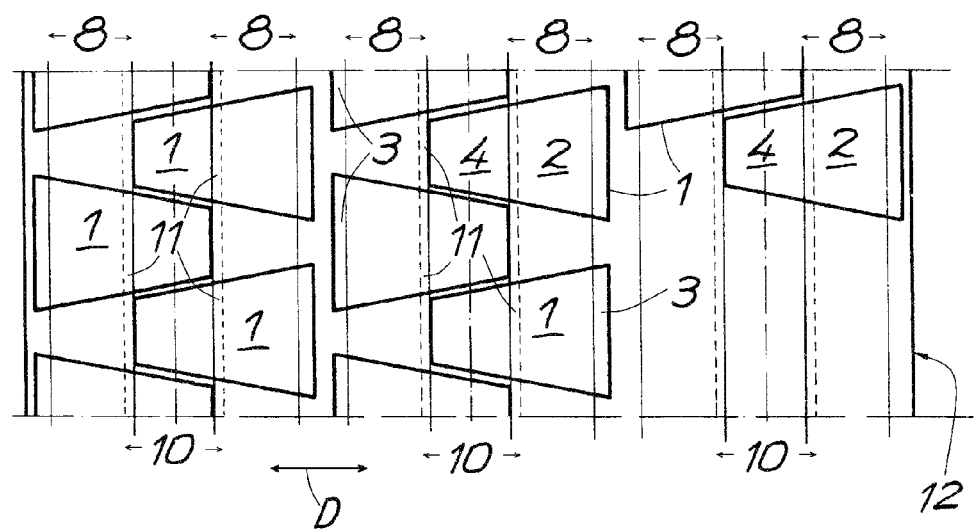
FIG. 2 is a top view of a textile web from which diaper closure elements as shown in FIG. 1 can be punched.

As seen in FIG. 1, a diaper closure element 1 according to the invention 1 has an elastic stretch region 2, an inelastic attachment region 3 for securing to a diaper, and a similarly inelastic and reinforced attachment region 4 for securing to a closure component 5. The diaper closure element is a laminate is having outer cover layers 6 and 7 of nonwoven and a punched-out piece of a film strip 8 of an elastic polymer laminated between the cover layers 6 and 7. The cover layers 6 and 7 are longer in a stretch direction D than the pieces of laminated elastic film strip 8, and are bonded to each other at projecting ends that form the inelastic attachment regions 3 and 4.

The first attachment region 3 for securing to a diaper is soft and flexible, and is only composed of two interconnected nonwoven layers 6 and 7. The second attachment region 4 for the closure component 5, on the other hand, is reinforced by a punched-out piece of a reinforcement film strip 10 that is bonded to the pieces of laminated elastic film strip 8 in overlap regions 11. These overlap region 11 are approximately 2 mm to 10 mm wide.

The reinforcement film strip 10 is composed of a polymer that is characterized by a substantially greater rigidity and greater tensile strength than the rigidity and tensile strength the elastic film strip 8. The elastic stretch region 2 of the diaper closure element 1 is activated by monoaxial stretching of the laminate. The locally restricted stretching causes fibers of the nonwoven layers 6 and 7 to be overstretched by the mechanical activation such that the resistance to elongation of the laminate is reduced in the region 2. The stretched region is shorter in the direction D than the elastic region 2 and terminates short of the overlap region 11 at its inner edge.

The diaper closure elements 11 are punched from a wide textile web 12 seen in top view in FIG. 2. In order to produce the textile web 12 shown in FIG. 2, parallel and spaced film strips 8 of an elastically stretchable polymer are laminated in pairs between the two nonwoven cover layers 6 and 7. In addition, strips 10 of the reinforcement film are inserted between the cover layers 6 and 7 and bridge the space each pair of two elastic film strips 8 and are glued along both edges at the overlap regions 11 to the elastic film strips 8 of the respective pair.

Figure 4:
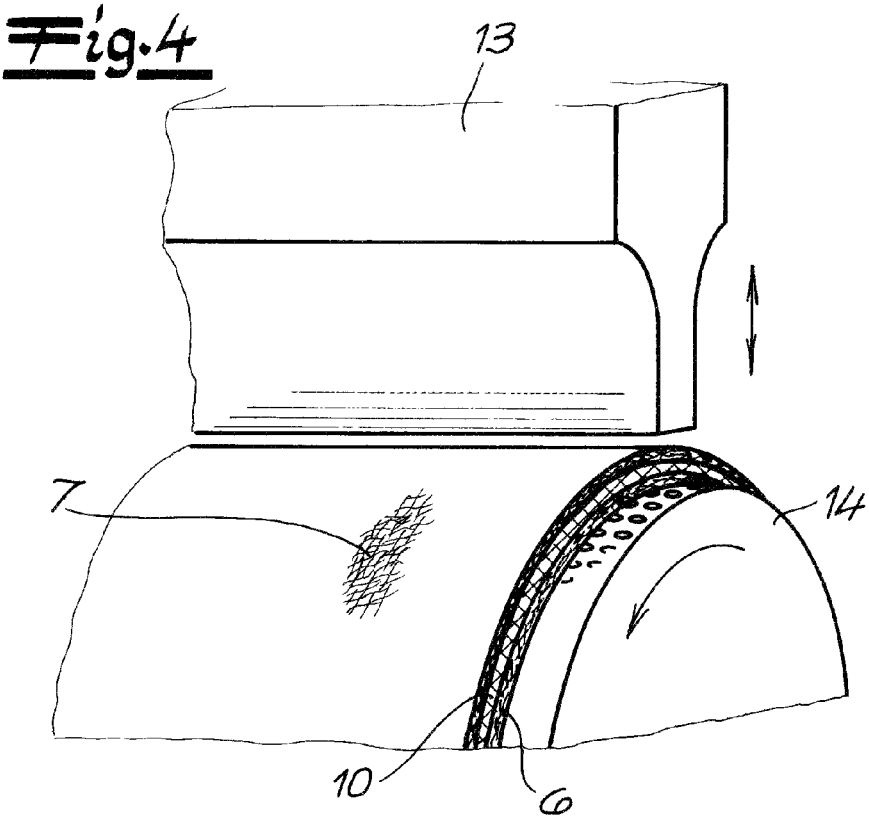
FIG. 4 shows a tool arrangement used to ultrasonically weld together textile layers shown in FIG. 3.
Figure 5:
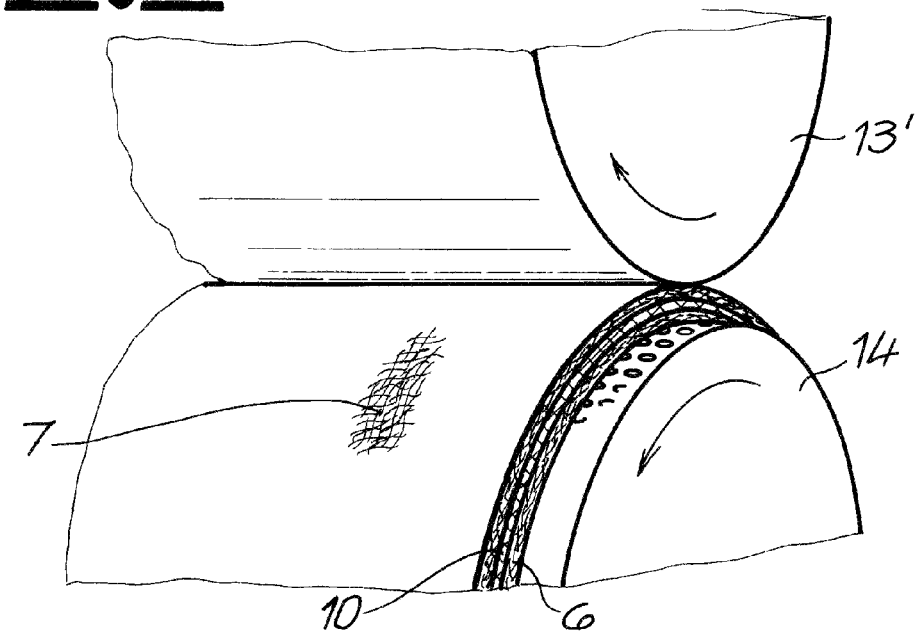
FIG. 5 shows an alternative tool arrangement used to ultrasonically weld together the textile layers shown in FIG. 3.

The cover layers 6 and 7 composed of nonwoven are bonded to the reinforcement film by ultrasonic welding. To accomplish this, the nonwoven cover layers 6 and 7 and the reinforcement film 10 are passed between a hot sonotrode 13 or 13' and a pixel roll 14 whose surface has a raised structure, bumps, and/or indentations. The tool arrangements for the ultrasonic welding are shown in FIGS. 4 and 5. A vertical sonotrode 13 having a smooth contact surface is used in the embodiment of FIG. 4. In the embodiment of FIG. 5, a cylindrical rotatable sonotrode 13' with a smooth outer surface is used.

An enlarged view of the layered structure of the textile web 12 in the inelastic and reinforced attachment region 4 is provided in FIG. 3. The reinforcement film 10 has a support layer 15 of polypropylene and an outer layers 16 of polyethylene on both faces. Both of the nonwoven cover layers 6 and 7 are composed of bicomponent fibers that have a core of polypropylene and a sheath of polyethylene. The nonwoven layer 6 and 7 are bonded by ultrasonic welding to the outer polyethylene layers 16 of the reinforcement films 10. The reinforcement film 10 is bonded by an adhesive along both edge overlap regions 11 to the elastic film strips 8. The elastic film strips 8 are in turn glued by stripes 17 of adhesive to the cover layers 6 and 7.

In the reinforcement film 10 in the embodiment of FIG. 6 the support layer 15 is composed of polypropylene and the outer layer 16 is of polyethylene and on only one side. The cover layer 6 that is bonded to the polyethylene layer of the reinforcement film 10 is in turn composed of bicomponent fibers that have a fiber core of polypropylene and a fiber sheath of polyethylene. The support layer 15 of the reinforcement film 10 is bonded to a nonwoven 7' composed of polypropylene fibers.

I claim:

1. A method of making a textile web from which can be punched elastically stretchable diaper closure elements that each comprise an inelastic and reinforced attachment region for securing a closure component and an adjacent elastic stretch region, the method comprising:
   inserting a plurality of pairs of elastic film strips of an elastically stretchable polymer between two cover layers of nonwoven with the film strips parallel and spaced laterally from one another;
   inserting between each pair of elastic film strips a strip of a reinforcement film that has a support layer and an outer layer of polyethylene on at least one side between the cover layers with each reinforcement-film strip overlapping each of the respective elastic film strips at a respective overlap region;
   bonding the reinforcement-film strips to the elastic film strips in the overlap regions; and
   bonding the nonwoven cover layers to the reinforcement film strips by ultrasonic or thermal welding, the cover layer bonded to the outer polyethylene layer of the reinforcement film is itself composed of bicomponent fibers that have a fiber core of polypropylene and a fiber sheath of polyethylene, the support layer of the reinforcement film being composed of a polymer that has a higher melting point than the polyethylene of the outer layer.

2. The method defined in claim 1, wherein the support layer is composed of a polypropylene.

3. The method defined in claim 2 wherein the polypropylene is polypropylene homopolymer, cycloolefin copolymer, styrene polymer, polyamide, polyactide, thermoplastic polyurethane, or blends thereof.

4. The method defined in claim 1, wherein the support layer of the reinforcement film strip is composed of a polypropylene and the nonwoven has polypropylene fibers.

5. The method defined in claim 1, wherein the reinforcement film strip is composed of a multilayer film that has the support layer as a core and an outer layer of polyethylene on both sides, the nonwoven cover layers being of bicomponent fibers that have a fiber core of polypropylene and a fiber sheath of polyethylene.

6. The method defined in claim 1, wherein the elastic film strips bonded to the cover layers by gluing.

7. The method defined in claim 6, wherein the reinforcement film is glued to the elastic film strips substantially only in the overlap regions.

8. The method defined in claim 1, wherein the reinforcement film is first bonded to at least one cover layer by adhesive applied in stripes and thereafter is permanently bonded to both cover layers by ultrasonic or thermal welding 9. The method defined in claim 1, wherein the ultrasonic welding is done by passing nonwoven cover layers and the reinforcement film between a sonotrode and a pixel roll whose surface has a structure of bumps and/or indentations.

10. The method defined in claim 8, wherein the sonotrode is upright and has a smooth contact surface.

11. The method defined in claim 8, wherein the sonotrode is cylindrical and rotatable.

* * * * *